United States Patent [19]
Vega et al.

[11] Patent Number: 6,001,885
[45] Date of Patent: Dec. 14, 1999

[54] RETINOID INHIBITION OF EXPRESSION OF VEGF

[75] Inventors: Barbara Vega, Nice; Serge Michel, Roquefort les Pins; Annie Ladoux; Christian Frelin, both of Nice, all of France

[73] Assignee: Centre International de Recherches Dermatologiques, Valbonne, France

[21] Appl. No.: 08/921,511

[22] Filed: Sep. 2, 1997

[30] Foreign Application Priority Data

Sep. 2, 1996 [FR] France .................................. 96 10685

[51] Int. Cl.⁶ ........................ A61K 31/07; A61K 31/075; A61K 31/165; A61K 31/19
[52] U.S. Cl. .......................... 514/725; 514/319; 514/345; 514/431; 514/448; 514/469; 514/534; 514/569; 514/622; 514/721
[58] Field of Search .................................... 514/725, 721, 514/622, 569, 534, 469, 448, 431, 345, 319

[56] References Cited

U.S. PATENT DOCUMENTS 4,888,342  12/1989  Kligman .................................. 514/419

FOREIGN PATENT DOCUMENTS

| 0698392 | 2/1996 | European Pat. Off. . |
|---|---|---|
| 92/13063 | 8/1992 | WIPO . |
| 94/17796 | 8/1994 | WIPO . |
| 94/20093 | 9/1994 | WIPO . |
| 95/33745 | 12/1995 | WIPO . |
| 96/23498 | 8/1996 | WIPO . |

OTHER PUBLICATIONS

J. Biol. Chem., vol. 269, No. 34, (1994), pp. 21440–21447.
Cancer Lett, vol. 73, No. 1, (1993), pp. 41–49.
Cancer Res., vol. 56, No. 7, (Apr. 1996), pp. 1571–1577.
Pol.J. Pharmacol., vol. 48, No. 3, (May–Jun. 1996), pp. 307–316.
Surber et al., Arzneik.–Forsch., 43 (90, 1001–4 (Abstract), 1993.
Oikawa et al. Eur. J. Pharmacol., 249 (1), 113–16 (Abstract), 1993.
Nagpal et al. L. Biol. Chem., 270(2), 923–7 (Abstract), 1995.
Crit. Rev. Oncol. Hematol, vol. 20, No. 1–2, Aug. 1995, pp. 9–39.
Breast Cancer Res. Treat., vol. 36, No. 2, 1995, pp. 139–155.
Proc. Annu. Meet. Assoc. Cancer Res., vol. 35, 1994, pp. 659–660.
Leuk. Lymphoma, vol. 11, No. 1–2, Sep. 1993, pp. 27–36.
J. Clin. Invest., vol. 93, No. 6, Jun. 1994, pp. 2490–2496.
J. Invest. Dermatol., vol. 96, No. 1, Jan. 1991, pp. 111–115.
Journal of Biological Chemistry, vol. 270, No. 2, Jan. 13, 1995, pp. 923–927.
Martindale, "The Extra Pharmacopoeia", Thirtieth Edition, Edited by James E. F. Reynolds, London, pp. 758–771 (1993).

*Primary Examiner*—Phyllis G. Spivack
*Attorney, Agent, or Firm*—Burns, Doane, Swecker & Mathis, L.L.P.

[57] ABSTRACT

The retinoids, in particular the anti-AP-1 retinoids, effectively inhibit the expression of VEGF, and thus are useful for the therapeutic treatment of disease states manifesting an overexpression of VEGF.

7 Claims, No Drawings

RETINOID INHIBITION OF EXPRESSION OF VEGF

BACKGROUND OF THE INVENTION

1. Technical Field of the Invention

The present invention relates to inhibiting the expression of VEGF by administration of retinoids, in particular anti-AP-1 (Activator Protein-1) retinoids. This invention also relates to the retinoid treatment of disease states manifesting an overexpression of VEGF, in particular psoriasis, Kaposi's syndrome, bullous dermatoses, tumors, metastases, angiomas, eczema, urticaria, cutaneous hypersensitivity type IV, rheumatoid arthritis, and contact allergies.

2. Description of the Prior Art

VEGF, or "Vascular Endothelial Growth Factor," is a 34–36 kDa homodimeric glycoprotein whose sequence reflects an approximately 20% identity with the A and B chains of PDGF (Tischer et al., *J. Biol. Chem.*, 266, 11947–11954 (1991)). The additional DNA sequence of VEGF codes for a signal peptide enabling it to be secreted in opposition to FGF (Fibroblast Growth Factor), which does not contain such a sequence in the structure of its gene. Because the major production sites and the action sites are different, VEGF acts principally in a paracrine mode. The presence of VEGF has been discovered in both numerous tumors and healthy tissue (D. L. Senger et al., *Cancer Metastasis Rev.*, 12, 303–324 (1993)).

In healthy skin, the expression of VEGF may be increased following an injury (L. F. Brown et al., *J. Exp. Med.*, 176, 1375–1379 (1992)). The overexpression of VEGF has also been determined in numerous skin diseases associated with vascular hyperproliferation and/or to vascular changes, as in psoriasis patches (M. Detmar et al., *J. Exp. Med.*, 180, 1141–1146 (1994)), in Kaposi's syndrome (K. Weindel et al., *Biochem. Biophys. Res. Commun.*, 183, 1167–74 (1992)), and in bullous dermatoses (L. F. Brown et al., *J. Invest. Dermatol.*, 104, 744–749 (1995)).

It is widely known that all-trans retinoic acid affects cell differentiation and/or proliferation by interacting with nuclear receptors, or sRAR (Retinoic Acid Receptors) contained in the cell nucleus. 9-cis retinoic acid also interacts with Retinoic X Receptors (sRXR). Numerous synthetic analogs exhibit biological activity similar to that of all-trans retinoic acid or 9-cis-retinoic acid. These compounds are generally designated "retinoids." Included among the retinoids are, more specifically, RAR agonists, which interact with the sRAR receptors; these include etretinate and adapalene. To date, there are three known subclasses of RAR receptors, termed $\alpha$-RAR, $\beta$-RAR, and $\gamma$-RAR. After fixation of a ligand (i.e., all-trans retinoic acid), these receptors interact with the region promoting genes regulated by retinoic acid in specific response elements (RARE).

Certain analogs may become fixed and may activate a subclass of RAR receptor ($\alpha$, $\beta$, or $\gamma$). Finally, other analogs elicit no specific selective activity with respect to these various receptors. In this regard, for example, all-trans retinoic acid activates the sRAR (sRAR specific agonist ligand) belonging to all subclasses.

Numerous dermatological diseases and/or disorders may entail poor regulation of the sRAR receptors. These diseases and/or disorders most often exhibit an inflammatory, allergic, and/or immunological component. Retinoic acid, and, retinoids such as etretinate and adapalene, are drug species used to treat acne. Retinoic acid has also been described as a therapeutic active agent for treating the signs of skin aging, whether chronological or photoinduced (U.S. Pat. No. 4,888,342).

Certain retinoids have been described as effective for regulating the expression of genes, such as keratins (M. Tomic-Canic et al., *J. Biol. Chem.*, 271, 1416–1423 (1996)) or for altering PDGF activity in psoriatic fibroblasts (F. Raynaud et al., *J. Invest. Dermatol.*, 96, 111–115 (1991)). And certain retinoids have also been demonstrated to exhibit anti-AP-1 activity, namely, they inhibit AP-1 activity (WO-95/33,745). To date, no effect elicited by retinoids on VEGF expression has been reported in the literature (see, for example, Harada et al., *J. Clin. Invest.*, 93, 2490–2496 (1993)).

SUMMARY OF THE INVENTION

It has now surprisingly been determined that retinoids, and, more specifically, retinoids exhibiting anti-AP-1 activity, inhibit VEGF expression in keratinocytes.

Briefly, the present invention thus features the use of at least one retinoid exhibiting anti-AP-1 activity in order to inhibit the in vitro expression of VEGF.

This invention also features the formulation of at least one retinoid exhibiting anti-AP-1 activity into drug compositions for the treatment of disease states or afflictions associated with an overexpression of VEGF. These disease states may affect various organs and tissues, and they may be cutaneous or ocular conditions. These afflictions include, most notably, psoriasis, Kaposi's syndrome, bullous dermatoses, tumors, metastases, angiomas, diabetic retinopathies, photoinduced aging, irritation dermatitis, eczema, urticaria, cutaneous hypersensitivity type IV, rheumatoid arthritis, and contact allergy.

Too, the present invention features a regimen for treating disease states associated with an overexpression of VEGF, according to which an effective amount of at least one retinoid exhibiting anti-AP-1 activity is administered to a mammalian subject in need of such treatment, such amount being sufficient to inhibit the expression of VEGF in the tissues or organs affected by VEGF overexpression.

DETAILED DESCRIPTION OF BEST MODE AND SPECIFIC/PREFERRED EMBODIMENTS OF THE INVENTION

More particularly according to the present invention, by the term "retinoid" are intended all compounds exhibiting a biological activity profile similar to that of all-trans retinoic acid or 9-cis-retinoic acid; these compounds may alter gene expression by means of receptors belonging to the retinoic acid group, such as sRAR and sRXR. Thus, the retinoids according to the invention may exhibit activity in tests of differentiation of mouse embryonic teratocarcinoma cells (F9) (*Cancer Research*, 43, p. 5268 (1983)) and/or in the test for inhibition of ornithine decarboxylase after induction by TPA in mice (*Cancer Research*, 38, pp. 793–901 (1978)). These tests reveal the activity of these compounds in the areas of cell differentiation and proliferation. The cell (F9)-differentiation test permits assessing sRARs agonist activity, such as antagonist activity with respect to the retinoic acid receptors. Indeed, an antagonist is inert when used alone in this test, but inhibits partially or totally the effect produced by an agonist retinoid on the morphology and secretion of the plasminogen activator. These compounds may, therefore, also exhibit activity in a test involving the identification of sRAR-antagonist molecules, as described in European Patent Application No. 0,749,755, assigned to the assignee hereof. Other retinoids according to the invention may be linked to sRXR receptors, certain of which elicit an agonist activity, others an antagonist activity. The binding and transactivation properties exhibited as agonist or antagonist to sRXR receptors are determined by conventional techniques well known to this art, for example: B. Martin et al., *Skin Pharmacol.*, 5, 57–65 (1992); M. T. Cavey et al., *Anal. Biochem*, 186, 19–23 (1990); Levin et al., *Nature*, 355, 359–61; Allenby et al., *Proc. Natl. Acad. Sci.*, 90, 30-4 (1993); Allenby et al., *J. Biol. Chem.*, 269, 16689–95 (1994).

Retinoids which are agonists of sRAR and of sRXR are the preferred. Even more preferably, sRAR-agonist retinoids are employed.

The retinoids according to the invention also exhibit anti-AP-1 activity. Such anti-AP-1 activity may be demonstrated using the techniques described in the literature, in particular the technique described in WO-95/33745. The anti-AP-1 activity of a compound may be assessed using transactivaton experiments in cells, such as HeLa cells, utilizing a portion of the collagenase promoter cloned above chloramphenicol acetyl transferase, either without co-transfection, thus using only endogenous receptors, or by co-transfection using an expression receptor coding for sRAR receptors.

Representative anti-AP-1 retinoids include the retinoids described in WO-95/33745, and those described, in particular, in EP-170,105, EP-199,636, EP-210,118, EP-210,929, EP-292,348, EP-409,728, EP-514,264, EP-514,269, EP-552,282, EP-568,898, EP-584,191, EP-658,553, EP-661,258, EP-679,630, EP-679,631, FR-2,677,020, FR-2,713,637, FR-2,713,635, FR-2,713,640, FR-2,719,044, FR-2,725,205, FR-2,726,274, FR-2,729,664, FR-2,731,706, FR-2,744,452, FR-2,746,101, FR-2,746,098, and DE-28,19,213.

Particularly exemplary anti-AP-1 retinoids, include the following compounds:

4-[(5,6,7,8-Tetrahydro-5,5,8,8-tetramethyl-2-naphthyl) carboxamido]benzoic acid (Compound 1);

6-[3-(1-Adamantyl)-4-methoxyphenyl]-2-naphthoic acid (Compound 2);

6-[3-(1-Adamantyl)-4-hydroxyphenyl]-2-naphthoic acid (Compound 3);

4-[(5,6,7,6-Tetrahydro-5,5,8,8-tetramethyl-2-anthracenyl)benzoic acid (Compound 4);

4-[-1-Hydroxy-(5,6,7,8-tetrahydro-5,5,8,8-tetramethyl-2-naphthyl)-2-propynyl]benzoic acid (Compound 5);

4-[2-(3-Adamantan-1-yl-4-methoxyphenyl)-2-oxoethoxy]-2-hydroxybenzoic acid;

2-Hydroxy-4-[2-oxo-2-(5,5,8,8-tetramethyl-5,6,7,8-tetrahydronapthalene-2-yl)-ethoxyl-benzaldehyde;

2-(3-Hydroxy-4-methylphenoxy)-1-(5,5,8,8-tetramethyl-5,6,7,8-tetrahydronaphthalene-2-yl)-ethanone;

N-Ethyl-2-hydroxy-4-(2-hydroxy-2-(5,5,8,8-tetramethyl-5,6,7,8-tetrahydronaphthalene-2-yl)-ethoxy]-benzamide;

2-[3-Hydroxy-4-(piperidine-1-carbonyl)-phenoxyl-1-(5,5,8,8-tetramethyl-5,6,7,8-tetrahydronaphthlene-2-yl)-ethanone;

3-Tert-butyl-4-methoxybenzoic acid-4-(4-hydroxyphenylcarbamoyl)-benzyl ester;

Methyl-4-[2-hydroxy-2-(5,6,7,8-tetrahydro-5,5,8,8-tetramethyl-2-naphthyl)acetamido]phenyl sulfone;

5-[(E)-2-(3,5,5,8,8-Pentamethyl-5,6,7,8-tetrahydronapthalene-2-yl)-propenyl]-thiophene-2-carboxylic acid;

4-(3,5,5,8,8-Pentamethyl-5,6,7,8-tetrahydronapthalene-2-yloxy)-propenyl]-benzoic acid;

6-(5,5,8,8-Tetramethyl-5,6,7,8-tetrahydroanthracene-2-carbonyl)-naphthalene-2-carboxylic acid;

4-[(E)-2-(3-(1-Methylcyclohexyl)-4-(6-tert-butoxycarbonylpentyloxyphenyl)ethenyl]-benzoic acid;

4-(4,4-Dimethylthiochroman-6-ylethynyl)-2-hydroxybenzoic acid methyl ester;

2-Nonyloxy-5-(5,5,8,8-tetramethyl-5,6,7,8-tetrahydroanthracene-2-yl)-benzoic acid;

2-Hexyloxy-4-(5,5,8,8-tetramethyl-5,6,7,8-tetrahydroanthracene-2-yl)-benzoic acid;

3-[(5,6,7,8-Tetrahydro-5,5,8,8-tetramethyl-2-naphthyl)(3-methyl)-2H-1-benzofuran]-6-carboxylic acid;

4-[6-Methyloxycarbonyl-7-(1-adamantyl)-2-naphthyl]benzoic acid;

4-[3-Adamantan-1-yl-4-(2-methoxy-ethoxymethoxy)-phenylethynyl]-2-hydroxybenzoic acid;

3-Methyl-3-(1,2,3,4-tetrahydro-1,4a,9b-trimethyl-1,4-methanodibenzofuran-8-yl)-2H-1benzofuran-6-carboxylic acid;

3-[(5,6,7,8-Tetrahydro-5,5,8,8-tetramethyl-2-naphthyl)(3-allyl)-2H-1benzofuran]-6-carboxylic acid;

2-Chloro-4-(3,5,5,8,8-pentamethyl-5,6,7,8-tetrahydro-2-naphthylthio)-benzoic acid;

4-[6-(4-Hydroxycarbonylbenzyloxy)-7-(1-adamantyl)-2-naphthyl]benzoic acid;

6-[3-Adamantan-1-yl-4-hydroxyphenyl]-naphthalene-2-carboxylic acid;

3-[[3-(3,5,5,8,8-Pentamethyl-5,6,7,8-tetrathydronaphthalene-2-yl)-phenyl]-acrylic acid;

6-(3,5,5,8,9-[Pentamethyl-5,6,7,8-tetrahydro-2-naphthylthio)-nicotinic acid;

4-[3-(5,6,7,8-Tetrahydro-5,5,8,8-tetramethyl-2-naphthyl)-1-propynyl]-salicylic acid;

4-(3,5,5,8,8-Pentamethyl-5,6,7,8-tetrahydro-2-naphthylthio)-benzoic acid;

2-Hydroxy-4-[3-hydroxy-3-(5,6,7,8-tetrahydro-5,5,8,8-tetramethyl-2-naphthyl)-1-propynyl]-benzoic acid.

The preferred compounds are the above compounds 1 to 5.

The drug species according to the invention may be formulated as pharmaceutical, and, in particular, dermatological, compositions.

The pharmaceutical compositions containing an effective amount of at least one retinoid exhibiting anti-AP-1 activity include an acceptable pharmaceutical vehicle, diluent or carrier therefor which is compatible with the mode of administration selected.

The appropriate amount, which obviously depends on the desired treatment and the nature of the compound selected, is thus determined by one skilled in this art.

The compounds according to the invention may be administered enterally, parenterally, systemically, topically, or to the eye.

Enterally, the composition, and more specifically the pharmaceutical composition, may be formulated as tablets, capsules, pills, syrups, suspensions, solutions, creams, ointments, powders, granulates, emulsions, microspheres or nanospheres, or lipid or polymeric vesicles permitting timed or delayed release. Parenterally, the composition, and more specifically the pharmaceutical composition, may be formulated as solutions or suspensions suitable for perfusion or injection.

The compounds according to the invention are characteristically administered in a daily dose of approximately 0.01 mg/kg to 100 mg/kg of body weight, taken 1 to 3 times per day.

Topically, the composition is a dermatological formulation and is, more particularly, intended for treatment of the skin and mucous membranes. It is formulated as ointments, creams, salves, buffers taken orally, solutions, gels, sprays, lotions, suspensions, and shampoos. It may also be formulated as microspheres or nanospheres, lipid or polymeric vesicles, or polymeric or hydrogel patches affording timed release. Such topical compositions may, moreover, be formulated in either anhydrous or aqueous form.

For application to the eyes, the subject compositions may be formulated as ophthalmic lotions, ointments, or gels.

The optical or eye composition contains at least one retinoid as indicated above in a concentration preferably ranging from 0.001% to 5% of the total weight of the composition.

The compositions according to the invention may also contain inert or even pharmacodynamically-active additives or adjuvants, or combinations of such additives and adjuvants, including, in particular, wetting agents; depigmenting agents such as hydroquinone, azelaic acid, caffeic acid or kojic acid; emollients; hydrating agents such as glycerol, PEG 400, thiamorpholinone and derivatives thereof, and urea; seborrhea- or acne-combating agents, such as S-carboxymethylcysteine, S-benzylcysteamine and the salts and derivatives thereof, and benzoyl peroxide; antibiotics such as erythromycin and esters thereof, neomycin, clindamycin and esters thereof, and tetracyclines; antifungal agents such as ketoconazole and 4,5-polymethylene-3-isothiazolidones; non-steroidal anti-inflammatory agents; carotenoids and, in particular, β-carotene; anti-psoriatic agents such as anthraline and derivatives thereof, and, lastly, 5,8,11,14-eicosatetraenoic and 5,8,11-eicosatrienoic acid and the esters and amides thereof.

The subject compositions may also contain flavor-enhancing agents, preservatives such as esters of parahydroxybenzoic acid, stabilizers, moisture-regulating agents, pH-regulating agents, osmotic pressure-adjustment agents, emulsifiers, UV-A and UV-B sunscreens, and antioxidants, such as α-tocopherol, butylhydroxyanisole, and butylhydroxytoluene, etc.

Inhibition of the expression of VEGF has been demonstrated for different retinoids by monitoring the expression of the mRNAs of VEGF in cultured normal human cells.

In order to further illustrate the present invention and the advantages thereof, the following specific examples are given, it being understood that same are intended only as illustrative and in nowise limitative.

EXAMPLES

The experimental protocol and the technique employed to determine the expression of VEGF were as follows:

Keratinocyte Culturing:

The cells were isolated from breast tissue and were seeded from a stock frozen during the first run in the "Keratinocyte Basal Medium" (KBM, Promocell). The following growth factors were present in the culture medium: bovine pituitary extract: 0.4% (v/v); epidermal growth factor: 10 ng/ml; and insulin: 5 μg/ml. When 80% of confluence was achieved, the culture medium was changed and the compounds diluted in DMSO were added over four hours. The control was produced by adding DMSO.

Expression of VEGF:

The keratinocytes were collected, then the total RNAs were extracted. A Northern blot was then carried out using the various RNA samples. The specific VEGF probe used was the VEGF 165 coding sequence. Glyceraldehyde Phosphate Dehydrogenase (GAPDH) was used as a reference, since the expression thereof does not vary as a function of the various treatments.

The expression of VEGF was thus calculated according to the ratio VEGF/GAPDH.

The results obtained for different retinoids as regards the expression of the mRNA of VEGF in normal human keratinocytes (NHK) are reported in Table I below:

TABLE I

| Compound | Concentration | Expression of VEGF |
|---|---|---|
| Control | $10^{-8}$ M | 100% |
| RA | $10^{-6}$ M | 70% |
| 1 | $10^{-8}$ M | 60% |
| 2 | $10^{-8}$ M | 58% |
| 3 | $10^{-7}$ M | 66% |
| 4 | $10^{-8}$ M | 76% |

RA = All-trans retinoic acid.

The activity of compound 5, a specific anti-AP-1 retinoid, was compared to the action of dexamethasone, a corticoid used to treat psoriasis, on NHK cultured as described above, the AP-1 complex being activated by the addition of $10^{-7}$ M TPA during a four-hour incubation time.

The results obtained are reported in Table II below:

TABLE II

| Compound | Concentration | Expression of VEGF |
|---|---|---|
| Control (without TPA) | — | 100% |
| TPA | — | 260% |
| TPA + compound 5 | $10^{-7}$ M | 169% |
| TPA + dexamethasone | $10^{-8}$ M | 120% |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for inhibiting VEGF expression in keratinocytes, comprising administering in a subject in need of such treatment an effective VEGF expression inhibiting amount of at least one retinoid.

2. The method as defined by claim 1, wherein said at least one retinoid exhibits anti-AP-1 activity.

3. The method as defined by claim 2, comprising administering to said mammalian organism from about 0.01 mg/kg to 100 mg/kg of body weight, per diem, of at least one anti-AP-1 retinoid.

4. The method as defined by claim 2, wherein said at least one retinoid comprising an sRAR or sRXR agonist.

5. The method as defined by claim 1, said at least one retinoid comprises 4-[(5,6,7,8-tetrahydro-5,5,8,8-tetramethyl-2-naphthyl)carboxamido]benzoic acid; 6-[3-(1-adamantyl)-4-methoxyphenyl]-2-naphthoic acid; 6-[3-(1-adamantyl)-4-hydroxyphenyl]-2-naphthoic acid; 4-[(5,6,7,6-tetrahydro-5,5,8,8-tetramethyl-2-anthracenyl)benzoic acid; 4-[-1-hydroxy-(5,6,7,8-tetrahydro-5,5,8,8-tetramethyl-2-naphthyl)-2-propynyl]benzoic acid; 4-[2-(3-adamantan-1-yl-4-methoxyphenyl)-2-oxoethoxy]-2-hydroxybenzoic acid; 2-hydroxy-4-[2-oxo-2-(5,5,8,8-tetramethyl-5,6,7,8-tetrahydronapthalene-2-yl)-ethoxyl-benzaldehyde; 2-(3- hydroxy-4-methylphenoxy)-1-(5,5,8,8-tetramethyl-5,6,7,8-tetrahydronaphthalene-2-yl)-ethanone; N-ethyl-2-hydroxy-4-(2-hydroxy-2-(5,5,8,8-tetramethyl-5,6,7,8-tetrahydronaphthalene-2-yl)-ethoxy]-benzamide; 2-[3-hydroxy-4-(piperidine-1-carbonyl)-phenoxyl-1-(5,5,8,8-tetramethyl-5,6,7,8-[tetrahydronaphthlene]tetrahydronaphthalene-2-yl)-ethanone; 3-tert-butyl-4-methoxybenzoic acid-4-(4-hydroxyphenylcarbamoyl)-benzyl ester; methyl-4-[2-hydroxy-2-(5,6,7,8-tetrahydro-5,5,8,8-tetramethyl-2-naphthyl)acetamido]phenyl sulfone; 5-[(E)-2-(3,5,5,8,8-pentamethyl-5,6,7,8-tetrahydronapthalene-2-yl)-propenyl]-thiophene-2-carboxylic acid; 4-(3,5,5,8,8-pentamethyl-5,6,7,8-tetrahydronapthalene-2-yloxy)-propenyl]-benzoic acid; 6-(5,5,8,8-tetramethyl-5,6,7,8-tetrahydroanthracene-2-carbonyl)-naphthalene-2-carboxylic acid; 4-[(E)-2-(3-(1-methylcyclohexyl)-4-(6-tert-butoxycarbonylpentyloxyphenyl)ethenyl]-benzoic acid; 4-(4,4-dimethylthiochroman-6-ylethynyl)-2-hydroxybenzoic acid methyl ester; 2-nonyloxy-5-(5,5,8,8-tetramethyl-5,6,7,8-tetrahydroanthracene-2-yl)-benzoic acid; 2-hexyloxy-4-(5,5,8,8-tetramethyl-5,6,7,8-tetrahydroanthracene-2-yl)-benzoic acid; 3-[(5,6,7,8-tetrahydro-5,5,8,8-tetramethyl-2-naphthyl)(3-methyl)-2H-1-benzofuran]-6-carboxylic acid; 4-[6-methyloxycarbonyl-7-(1-adamantyl)-2-naphthyl]benzoic acid; 4-[3-adamantan-1-yl-4-(2-methoxy-ethoxymethoxy)-phenylethynyl]-2-hydroxybenzoic acid; 3-methyl-3-(1,2,3,4-tetrahydro-1,4a,9b-trimethyl-1,4-methanodibenzofuran-8-yl)-2H-1benzofuran-6-carboxylic acid; 3-[(5,6,7,8-tetrahydro-5,5,8,8-tetramethyl-2-naphthyl)(3-allyl)-2H-1benzofuran]-6-carboxylic acid; 2-chloro-4-(3,5,5,8,8-pentamethyl-5,6,7,8-tetrahydro-2-naphthylthio)-benzoic acid; 4-[6-(4-hydroxycarbonylbenzyloxy)-7-(1-adamantyl)-2-naphthyl]benzoic acid; 6-[3-adamantan-1-yl-4-hydroxyphenyl]-naphthalene-2-carboxylic acid; 3-[[3-(3,5,5,8,8-pentamethyl-5,6,7,8-tetrahydronaphthalene-2-yl)-phenyl]-acrylic acid; 6-(3,5,5,8,9-[pentamethyl-5,6,7,8-tetrahydro-2-naphthylthio)-nicotinic acid; 4-[3-(5,6,7,8-tetrahydro-5,5,8,8-tetramethyl-2-naphthyl)-1-propynyl]-salicylic acid; 4-(3,5,5,8,8-pentamethyl-5,6,7,8-tetrahydro-2-naphthylthio)-benzoic acid; or 2-hydroxy-4-[3-hydroxy-3-(5,6,7,8-tetrahydro-5,5,8,8-tetramethyl-2-naphthyl)-1-propynyl]-benzoic acid.

6. The method as defined by claim 5, wherein said at least one retinoid comprises 4-[(5,6,7,8-tetrahydro-5,5,8,8-tetramethyl-2-naphthyl)carboxamido]benzoic acid; 6-[3-(1-adamantyl)-4-methoxyphenyl]-2-naphthoic acid; 6-[3-(1-adamantyl)-4-hydroxyphenyl]-2-naphthoic acid; 4-(5,6,7,8-tetrahydro-5,5,8,8-tetramethyl-2-anthracenyl)benzoic acid; or 4-[-1-hydroxy-(5,6,7,8-tetrahydro-5,5,8,8-tetramethyl-2-naphthyl)-2-propynyl]benzoic acid.

7. A method for inhibiting, the in vitro expression of VEGF comprising adding to an in vitro culture comprising keratinocytes, an amount of at least one retinoid effective to inhibit VEGF expression.

* * * * *